US011700843B2

(12) United States Patent
Zha et al.

(10) Patent No.: US 11,700,843 B2
(45) Date of Patent: Jul. 18, 2023

(54) SYSTEMS AND METHODS FOR DYNAMIC RELEASE PLANNING FOR INSECT RELEASE

(71) Applicant: Verily Life Sciences LLC, South San Francisco, CA (US)

(72) Inventors: Tiantian Zha, South San Francisco, CA (US); Peter Massaro, San Carlos, CA (US); Erika Lee, San Mateo, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 1088 days.

(21) Appl. No.: 16/193,416

(22) Filed: Nov. 16, 2018

(65) Prior Publication Data
US 2019/0141947 A1 May 16, 2019

Related U.S. Application Data

(60) Provisional application No. 62/587,092, filed on Nov. 16, 2017.

(51) Int. Cl.
*A01M 1/02* (2006.01)
*G01C 21/34* (2006.01)
(Continued)

(52) U.S. Cl.
CPC ........... *A01M 1/026* (2013.01); *A01K 67/033* (2013.01); *G01C 21/3453* (2013.01);
(Continued)

(58) Field of Classification Search
CPC ... A01K 67/033; A01M 1/026; G06Q 10/047; G06C 21/3453; G06C 21/3407
(Continued)

(56) References Cited

U.S. PATENT DOCUMENTS 5,005,416 A * 4/1991 Vick ..................... G01V 1/001
73/587
5,751,576 A * 5/1998 Monson .............. A01B 79/005
239/161
(Continued)

FOREIGN PATENT DOCUMENTS

| WO | WO-2009067089 A1 * | 5/2009 | ........... A01K 67/033 |
| WO | 2017154003 | 9/2017 | |
| WO | WO-2017154004 A1 * | 9/2017 | ........... A01K 67/033 |

OTHER PUBLICATIONS

A. Meats et al., "Dispersion theory and the sterile insect technique: application to two species of fruitfly," Entomologia Experimentalis et Applicata, 119:247-254 (2006) (Year: 2006).*

(Continued)

*Primary Examiner* — Joshua J Michener
*Assistant Examiner* — Henry Hooper Mudd
(74) *Attorney, Agent, or Firm* — Kilpatrick Townsend & Stockton LLP

(57) ABSTRACT

One example method includes receiving information indicating a population of wild insects within a geographic region; determining a number of wild insects per unit area within the geographic region; placing, based on the number of wild insects per unit area, one or more insect release points based on the number of wild insects per unit area, each insect release point indicating a release of a predefined quantity of insects; and generating an insect release route through the geographic region, the insect release route passing through each insect release point.

25 Claims, 10 Drawing Sheets

(51) Int. Cl.
*A01K 67/033* (2006.01)
*G06Q 10/047* (2023.01)
*G06Q 50/00* (2012.01)

(52) U.S. Cl.
CPC ........... *G06Q 10/047* (2013.01); *G06Q 50/00* (2013.01); *G01C 21/3407* (2013.01)

(58) Field of Classification Search
USPC .................................. 119/6.5; 705/7.11, 7.12
See application file for complete search history.

(56) References Cited

U.S. PATENT DOCUMENTS

| | | | |
|---|---|---|---|
| 7,317,399 B2* | 1/2008 | Chyun .................. | A01M 1/026 43/132.1 |
| 7,509,770 B2* | 3/2009 | Gardner, Jr. .......... | A01M 23/00 43/107 |
| 7,656,300 B2 | 2/2010 | Roennau | |
| 8,408,164 B2* | 4/2013 | Robinson, Jr. ....... | A01K 67/033 119/6.5 |
| 8,504,234 B2 | 8/2013 | Anderson | |
| 8,967,029 B1 | 3/2015 | Calvert | |
| 9,086,289 B2* | 7/2015 | Johnson .................. | G06F 16/29 |
| 11,147,256 B2* | 10/2021 | Dlamini .................. | G16H 40/67 |
| 2006/0150470 A1 | 7/2006 | Ronnau | |
| 2007/0176757 A1* | 8/2007 | Chyun ..................... | G01V 8/20 340/146.2 |
| 2012/0017834 A1 | 1/2012 | Holland et al. | |
| 2013/0144670 A1* | 6/2013 | Kickbusch ............. | G06Q 10/06 705/7.12 |
| 2013/0311215 A1* | 11/2013 | Rothley ................. | G06Q 10/08 705/7.11 |
| 2014/0303814 A1 | 10/2014 | Burema et al. | |
| 2016/0150744 A1* | 6/2016 | Lin ...................... | A01M 31/002 43/132.1 |
| 2017/0360027 A1* | 12/2017 | Vilinskis ................ | G06Q 10/10 |
| 2018/0206465 A1* | 7/2018 | Massaro ............... | A01K 67/033 |
| 2018/0295831 A1* | 10/2018 | Reid ....................... | A01M 1/20 |
| 2018/0299842 A1* | 10/2018 | Reid ....................... | A01M 1/20 |
| 2019/0082650 A1* | 3/2019 | Lepek ................... | A01M 1/026 |

OTHER PUBLICATIONS

Danilo O. Carvalho et al., "Suppression of a Field Population of Aedes adgypti in Brazil by Sustained Release of Transgenic Male Mosquitoes," PLOS Neglected Tropical Diseases, 9(7) (available at https://journals.plos.org/plosntds/article?id=10.1371/journal.pntd.0003864) (Year: 2015).*
European Application No. 18878768.3, Extended European Search Report, dated Jun. 18, 2021, 8 pages.
International Application No. PCT/US2018/061457, "International Search Report and Written Opinion", dated Feb. 1, 2019, 7 pages.
Singapore Application No. 11202003633S, Written Opinion, dated Sep. 9, 2021, 6 pages.
SG11202003633S, "Further Written Opinion", dated Dec. 15, 2022, 10 pages.

* cited by examiner

SYSTEMS AND METHODS FOR DYNAMIC RELEASE PLANNING FOR INSECT RELEASE

CROSS-REFERENCE TO RELATED APPLICATIONS

This application claims priority to U.S. Provisional Patent Application No. 62/587,092, titled "Systems and Methods for Dynamic Release Planning for Insect Release," filed Nov. 16, 2017, which is hereby incorporated by reference in its entirety.

FIELD

The present disclosure generally relates to population control of wild insects and more specifically relates to systems and methods for dynamic release planning for insect release.

BACKGROUND

All continents except *Antarctica* suffer from the plague of mosquito-vectored diseases. Various techniques for the control of mosquito populations involve the generation of sterile male insects for release into the wild for mating with local females. These techniques require systems for releasing the reared insects into the wild.

SUMMARY

Various examples are described for systems and methods for dynamic release planning for insect release. One example method includes receiving information indicating a population of wild insects within a geographic region; determining a number of wild insects per unit area within the geographic region; placing, based on the number of wild insects per unit area, one or more insect release points based on the number of wild insects per unit area, each insect release point indicating a release of a predefined quantity of insects; and generating an insect release route through the geographic region, the insect release route passing through each insect release point.

In another example, a non-transitory computer-readable medium includes processor-executable instructions configured to cause a processor to receive information indicating a population of wild insects within a geographic region; determine a number of wild insects per unit area; place, based on the number of wild insects per unit area, one or more insect release points based on the number of wild insects per unit area, each insect release point indicating a release of a predefined quantity of insects; and generate an insect release route through the geographic region, the insect release route passing through each insect release point.

In a further example, a system includes a non-transitory computer-readable medium; and a processor configured to execute processor-executable instructions stored in the non-transitory computer-readable medium, the processor-executable instructions configured to cause a processor to receive information indicating a population of wild insects within a geographic region; determine a number of wild insects per unit area; place, based on the number of wild insects per unit area, one or more insect release points based on the number of wild insects per unit area, each insect release point indicating a release of a predefined quantity of insects; and generate an insect release route through the geographic region, the insect release route passing through each insect release point.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
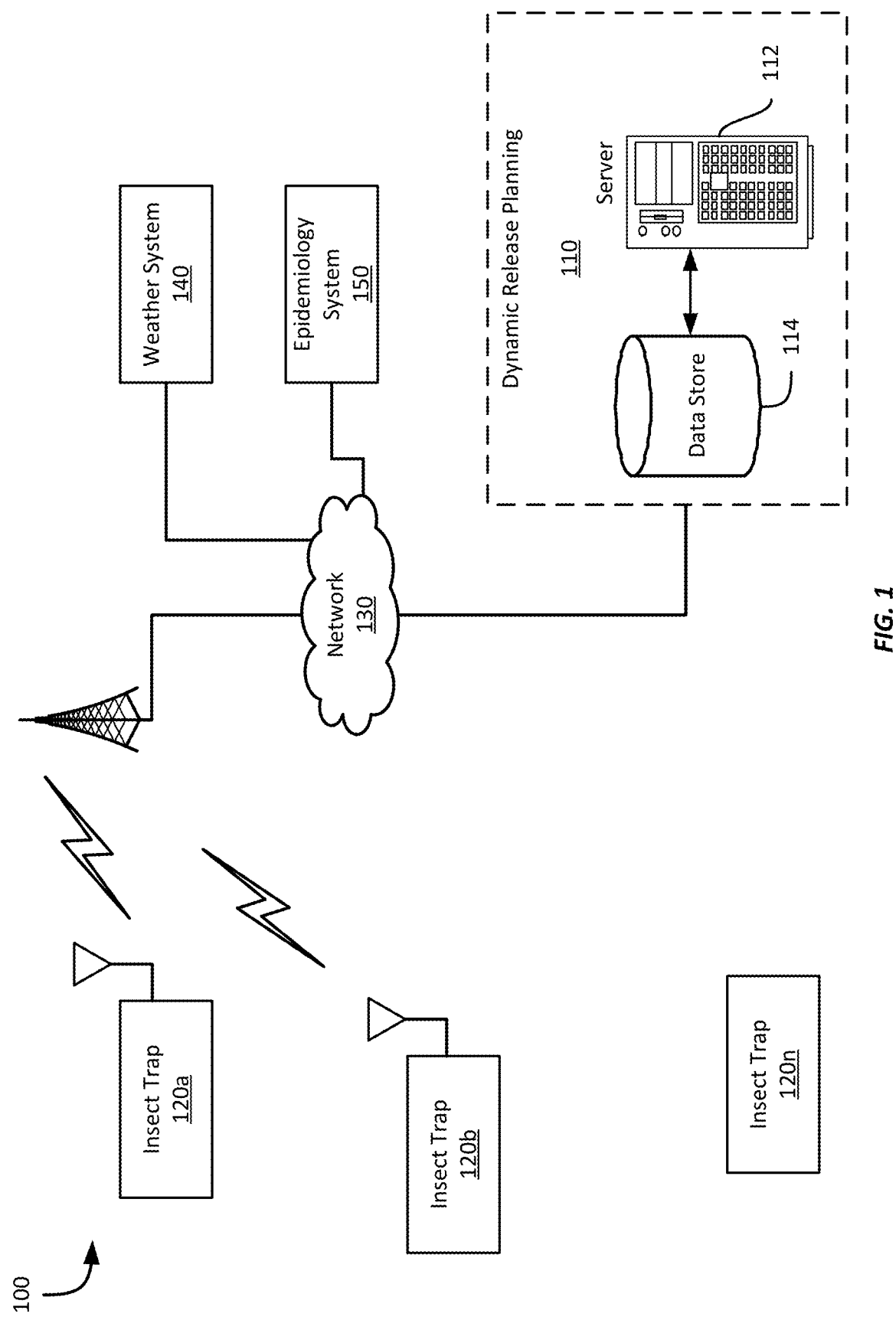
FIG. 1 shows an example system for dynamic release planning for insect release.

Examples are described herein in the context of systems and methods for dynamic release planning for insect release. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

A commercial insect rearing program may raise modified insects for use in controlling a local insect population. For example, the rearing program may engineer mosquitos with desirable traits. These desirable traits may include sterility (or otherwise lacking the ability to produce viable offspring) and the capability of competing with wild insects of the same species. In some examples, the reared insects may be male insects, e.g., sterile male mosquitos that are able to compete with wild mosquitos in the area for mating partners. Other desirable traits may include, for example, longevity, size, flight capability, or heat-resistance. Once reared, these modified mosquitos must be released into the wild to compete with local mosquitos for mating partners, which may thereby reduce the number of offspring and reduce the overall mosquito population.

To increase the efficacy of such a technique, the modified insects are released at particular locations and in quantities based on the wild insect population at those locations. Information about wild insect populations may be obtained from insect traps positioned throughout a region, which may then be provided to a software release planning tool. The release planning tool obtains the insect trap information and determines a wild female insect population based on the number of insects caught in each of the traps over a period of time. The wild female insect population is then used to determine a number of sterile male insects to be released into the geographic region to help reduce the total wild population. In this example, the release planning tool uses a predetermined ratio of ten sterile male insects per wild female insect to determine the number of sterile male insects to release along the route.

Next, the release planning tool identifies houses along roadways within the geographic region and road segments corresponding to each house. For example, a road segment may correspond to a house if the house's address has the same name as the adjacent road or if the house's driveway connects to the particular road segment. The road segment may be defined as a portion of a road between two cross streets, or a portion of road having a predetermined length, e.g., one tenth of a mile. Thus, for each house, a corresponding road segment is determined.

The system then determines an insect release route through the geographic region that traverses the entire region, e.g., all of the road segments within the region, or a portion of the geographic region that is within a predefined distance, e.g., 200 yards, of at least one insect trap. The system then assigns insect release points along the route.

To do so, in this example, the insect release tool determines a number of houses per road segment and assigns a weight to the road segment based on the number of houses associated with that road. After which, the release planning tool evenly distributes release points along the road segments based on the respective weights. Thus, release points for each road segment may be centered within the road segment, or may divide a road segment into equally sized portions. For example, if a road segment has two release points, the release planning tool may divide the road segment into thirds, and place two release points on the road segment to establish each of the thirds. Thus, it may equally divide release points within the road segments, though spacing between release points may vary over the course of the entire route.

The route information, which includes the release point information, may then be provided to an insect release vehicle, such as a truck or car that has been equipped with insect release mechanisms. The release vehicle then travels to a start-point of the insect release route and initiates the insect release route. During the course of traversing the insect release route, the route information prompts the driver regarding directions to follow the route as well as to initiate the release of insects at different locations along the route. Thus, the driver is able to release the appropriate number of mosquitoes at different locations along the route. Further, the driver may vary the rate at which insects are released based on the route information.

The process may then be iterated, with the software release planning tool updating the route and insect release points on subsequent days based on additional information obtained from the various traps, such as survivability of the sterile male insects, the change in wild female insect population, weather information (e.g., wind or rain), etc. Thus, during the course of treating an area, the software release planning tool may modify the release route, the release locations, or the rates of release at various locations as new data wild insect population information becomes available. Thus, the sterile male insects may be released more efficiently based on the actual conditions present within an area.

This illustrative example is given to introduce the reader to the general subject matter discussed herein and the disclosure is not limited to this example. The following sections describe various additional non-limiting examples and examples of systems and methods for dynamic release planning for insect release.

Referring now to FIG. 1, FIG. 1 shows an example insect release planning system 100. The system 100 includes a dynamic release planning system 110, which includes one or more servers 112 that are in communication with a data store 114. The system 100 also includes multiple insect traps 120a-n ("n" indicates any positive integer). Each of the insect traps 120a-n is positioned within a geographic region of interest and captures insects over a period of time. The types and number of captured insects can be obtained from each of the traps 120a-n and provided to the dynamic planning system 110, which stores the trap information in the data store 114.

In this example, two of the traps 120a-b are configured to autonomously identify and count insects of a predetermined type, such as mosquitos. Further, the predetermined type (or types) of insects may include differentiating based on the gender or whether the trapped insect is a wild insect or from a population of lab-raised insects, e.g., sterile male insects. For each captured and recognized mosquito, for example, the respective trap 120a-b increments a corresponding counter, such as a counter for wild female mosquitoes or a counter for sterile, lab-raised male mosquitoes, and also logs the time at which the insect was captured. The traps 120a-b then periodically provide sensor information to the dynamic release planning system 110. For example, the traps 120a-b may provide sensor information every 24 hours, or after a predetermined number of insects of interest have been captured. In this example, the traps 120a-b communicate wirelessly with the dynamic release planning system 110 using cellular communications techniques, but any suitable wireless communication techniques may be employed, including WiFi, BlueTooth ("BT"), BT low energy ("BLE"), code division multiple access ("CDMA"), frequency division multiple access ("FDMA"), time division multiple access ("TDMA"), or other known signals that are used to communicate within a wireless, cellular, or internet of things ("TOT") network, such as a system utilizing 3G, 4G or 5G, or further implementations thereof, technology.

In addition to traps 120a-b, trap 120n is manually inspected and the person inspecting the trap counts the number and types of insects of interest and provides the count(s) to the dynamic release planning system 110, such as using a smartphone or tablet, or by manually entering the sensor information directly into the dynamic release planning system and storing it in the data store 114. Thus, sensor information from one or more insect traps 120a-n may be obtained in a variety of different ways, depending on the capabilities of the traps in different examples of insect release planning systems.

In some examples the dynamic release planning system 110 may obtain information from other sources in addition to the traps 120a-n. In this example, the dynamic release planning system 110 is in communication with a weather reporting system 140 and an epidemiology system 150. The weather reporting system 140 provides information about a geographic region of interest, such as a region in which modified insects are to be released. In some examples, the dynamic release planning system 110 may obtain current, past, or predicted weather information for a region, including temperature information, humidity information, precipitation information, wind information, etc. Such information may be employed by the dynamic release planning system 110 to generate an insect release plan for a region. In addition, or instead, the dynamic release planning system 110 may also receive epidemiology information from the epidemiology system 150. Epidemiology information may include presence of one or more communicable diseases carried by insects within a region, a prevalence of such carrier insects, etc. Epidemiology information may be obtained from one or more hospitals, a governmental organization (e.g., the Centers for Disease Control), a university, etc. Such information may be employed by the dynamic release planning system 110 to increase a concentration of released modified insects in a region.

Figure 2:
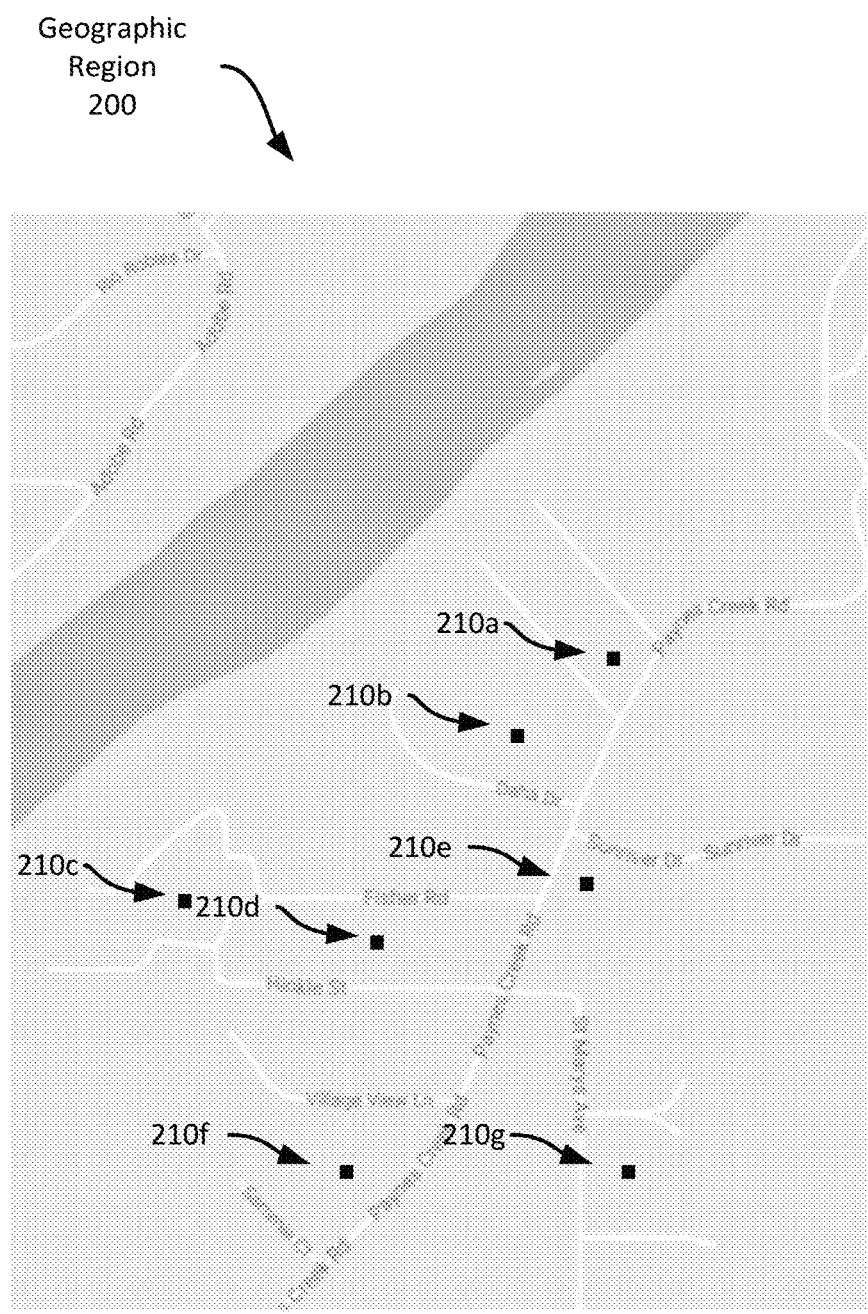
FIG. 2 shows an example geographic region having insect traps.

Referring now to FIG. 2, FIG. 2 shows a geographic region 100 having multiple insect traps 210a-g dispersed within it. Each of the traps 210a-g captures insects and provides information regarding the number and types of insects captured. In some examples, the traps 210a-g are autonomous and wirelessly report sensor information, while in some examples, the traps 210a-g are manually inspected and the insect information is manually gathered. In this example, each of the traps 210a-g transmits a wireless signal, e.g., a cellular signal, with information about insects captured by the respective trap to a remote computing device, which stores the information. The transmitted information in this example indicates a number of insects captured of a specified type (or types), such as mosquitos, as well as time information, such as a time stamp associated with the time of transmission, or time stamps associated with the capture of individual insects.

Figure 3:
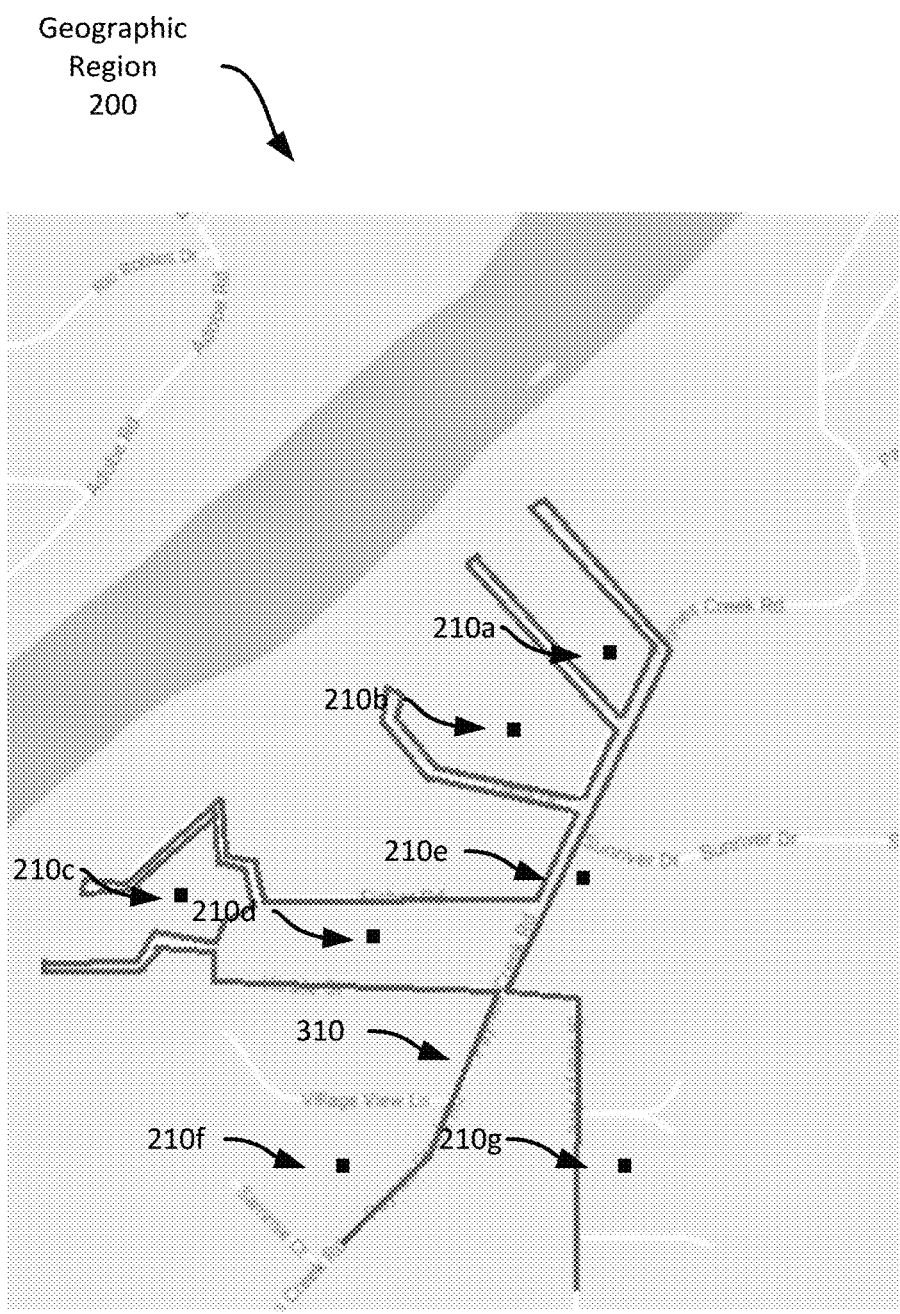
FIG. 3 shows an example geographic region having insect traps and an insect release route for an insect release vehicle.

Referring now to FIG. 3, FIG. 3 shows the geographic region 100 shown in FIG. 2, but with a route 310 overlaid on the streets running through the geographic region. The route 310 is provided to an insect release vehicle that will traverse the route 310 and release insects at different locations along the route 310. In the example shown in FIG. 3, the route 310 does not have any release points, but instead merely represents the route 310 that the release vehicle will take.

Figure 4A:
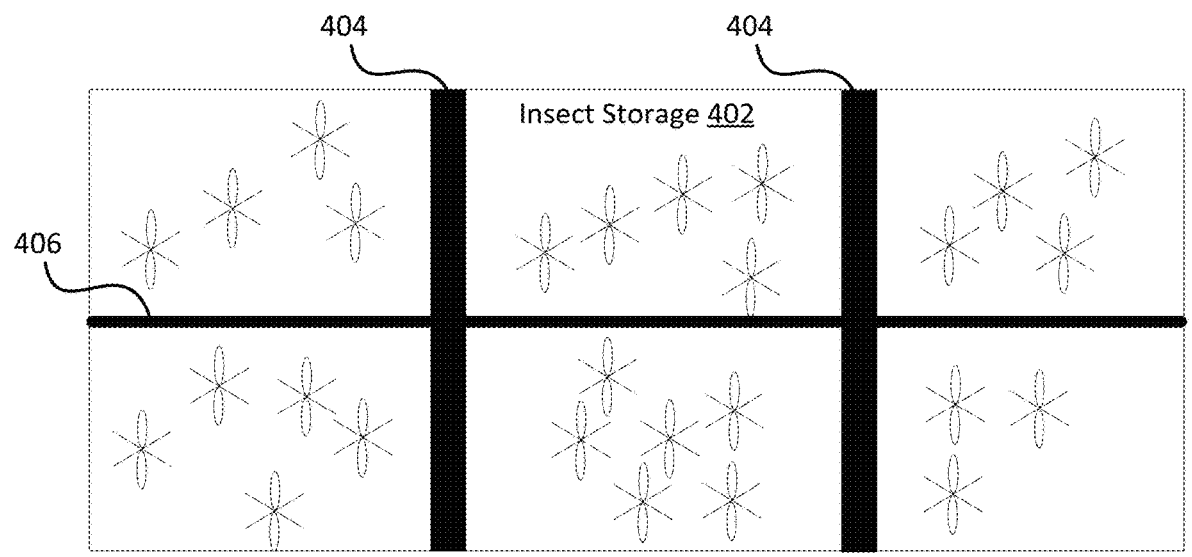
FIGS. 4A-4B show an example insect storage and release system.
Figure 4B:
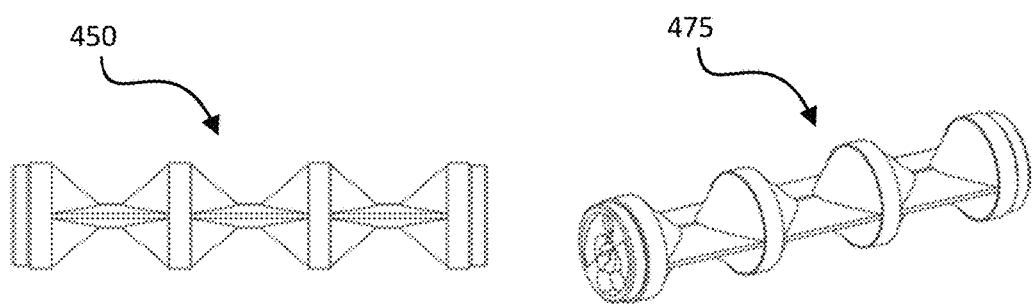
Figure 5:
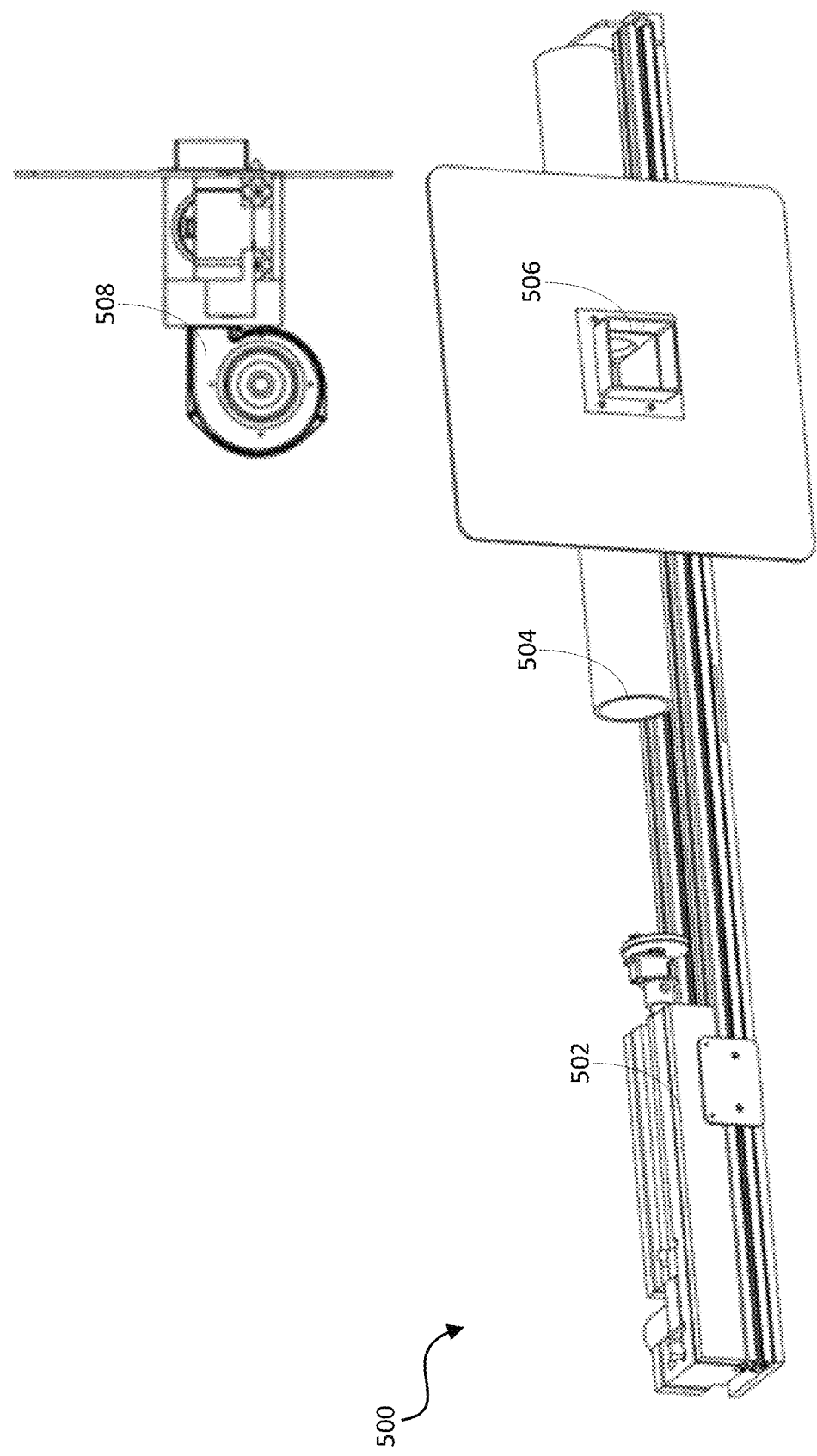
FIG. 5 shows an example insect release mechanism.

A release vehicle according to this disclosure may be any vehicle from which a population of modified insects may be released into an environment. Suitable vehicles may include cars, trucks, buses, motorcycles, bicycles, aircraft, etc. Release vehicles may be equipped with one or more insect release systems that store a population of insects and can release the insects. Release from an insect release system may be performed in one mass release, such as by opening a single door into an insect storage area. In some examples, however, insects may be released at a controlled rate to more precisely release insects into an environment according to a release plan generated by a dynamic release planning system 110 based on sensor information obtained from one or more insect traps 120*a-n*.

Referring now to FIG. 4A, FIG. 4A shows an example insect storage container 402 that may be used to release insects from a release vehicle. As shown in FIG. 4A, the insect storage container 402 comprise a plurality of dividers 404 that create a plurality of enclosed areas. In some embodiments, each of these enclosed areas may be of a different size. Each of these enclosed areas includes one or more insects, which may comprise one or more species of mosquitos. In some embodiments, each of the enclosed areas may comprise different numbers, types, or genders of insects. Further, each of the dividers is interconnected by a shaft 406. In some embodiments, a mechanism, described in more detail with respect to FIG. 5 below, may move this shaft forward or backward, thus moving the location of each compartment within insect storage 402.

Turning now to FIG. 4B, which shows additional example perspectives of dividers 450 and 475 that may be found in insect storage 402. As shown in FIG. 4B, each of the dividers 450, 475 comprises areas on which one or more mosquitos may roost. Further, each divider 450, 475 is interconnected, and thus may be pushed forward or backward together. In some embodiments, the dividers 450, 475 may further comprise compartments for sugar feeding and air circulation to help maintain the fitness of the insects prior to release. In some embodiments, the dividers 450, 475 are constructed of material to provide roosting space for insects. Some example materials for dividers 450, 475 include: mesh, sandblasted plastic, or perforated steel.

The embodiments shown in FIG. 4B are examples. In other embodiments, different shapes and/or form factors may be used to maximize one or more of: roosting area, air flow, storage space, and/or ability to release insects without damage.

The examples shown in FIG. 4A-4B may be employed to effect controlled release of quantities of insects at a desired rate. As discussed above, the insect storage container 402 is divided into multiple segments. Each segment may release insects independently of other segments, thus allowing a portion of the total insect population to be released at a particular time, rather than releasing the entire insect population.

Turning now to FIG. 5, which shows an example system 500 for automated mass release of insects. The system 500 shows one example embodiment of a loading mechanism 502, insect storage 504, and release mechanism 506.

As shown in FIG. 5, the loading mechanism 502 comprises a mechanism, such as a piston or solenoid to push or pull on a structure (e.g., one of the structures described above with regard to FIG. 4A or 4B) that may be positioned inside insect storage 504 to create enclosures for storing insects. The loading mechanism pushes the structure into a position such that the chamber it creates is positioned opposite (e.g., in front of) opening 506.

The opposite side of opening 506 includes blower 508, which is shown in a perspective view. The blower 508 may comprise one or more types of electric fans, e.g., a box fan, axial fan, centrifugal fan, radial fan, cross flow fan, bellows, or any other system known in the art for generating an air pressure differential. The blower 508 provides air pressure that forces insects out of the insect storage 504 via opening 506. In other embodiments, additional forms of pressure may be used, e.g., compressed air or carbon dioxide, or some other type of compressed gas to provide pressure to force insects out of insect storage 504.

The example release system 500 shown in FIG. 5 may be used in some examples to effect a controlled release of insects from one or more example insect storage containers, such as the insect storage containers shown in FIGS. 4A-4B. To control the release of the insect population, a segment of a storage container may be moved using by the example system 500 to expose a segment to the environment via the opening 506. The blower 508 may be employed to force insects out of the segment through the opening 506. Thus, by modifying the blower speed or the amount of a particular segment exposed to the opening, an insect release rate may be dynamically adjusted to release a desired quantity of insects over a predetermined period of time or distance. However, different examples according to this disclosure may employ any suitable insect release mechanism, including an augur to force insects to traverse a release tube, or gravity may be employed to release a release container or simply eject insects into the atmosphere.

Figure 6:
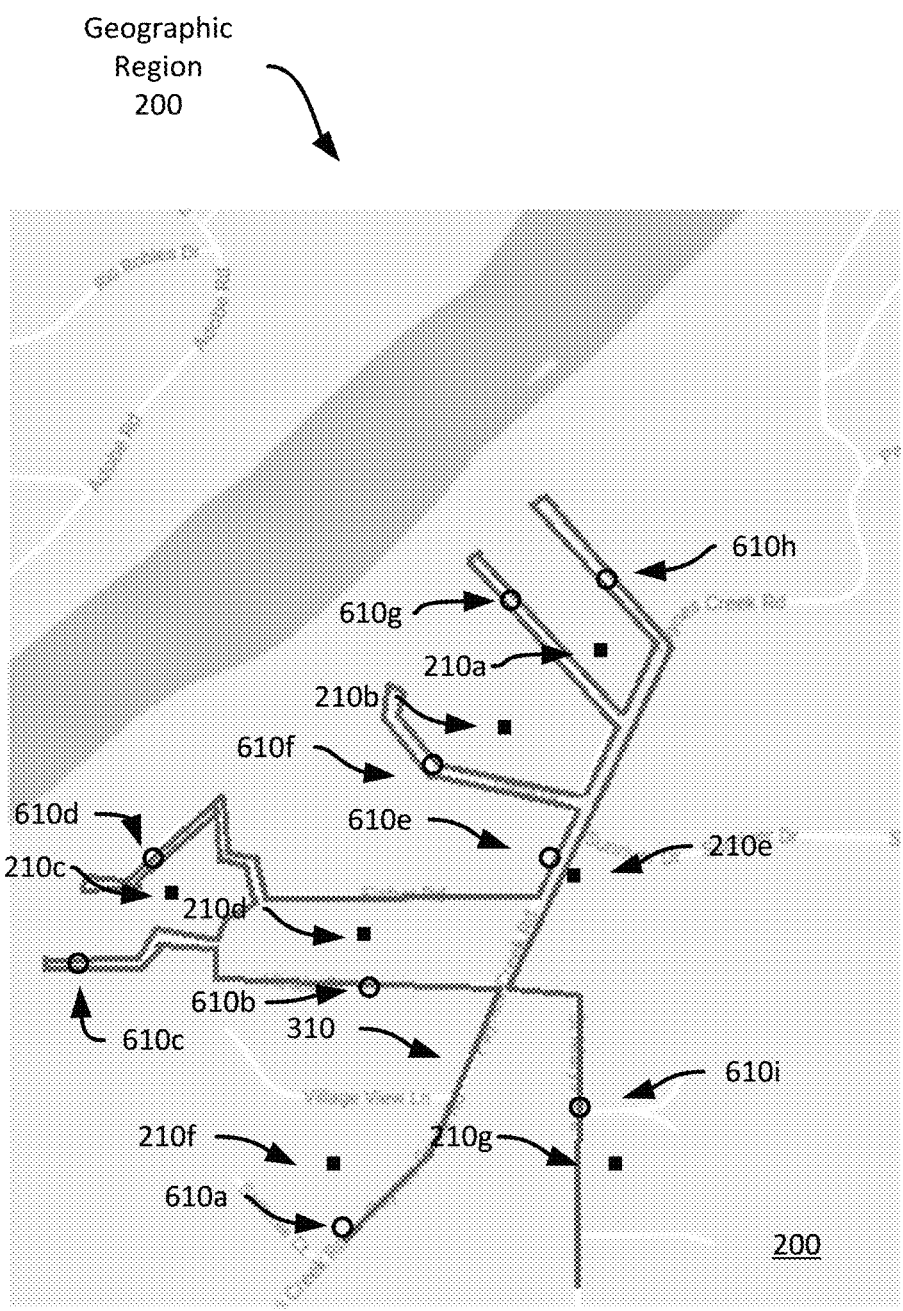
FIG. 6 shows an example geographic region having insect traps, an insect release route for an insect release vehicle, and multiple insect release points.

Referring now to FIG. 6, FIG. 6 shows the geographic region shown in FIGS. 1-2. In FIG. 6, however, the dynamic release planning system 110 has generated multiple insect release points 610a-i and positioned them along the route 310 to be taken by the release vehicle. In this example, the release points 610a-i each represent the release of the same number of modified insects, e.g., 5000 per release point or two segments of an insect container per release point. In addition, each release point has associated with it a release rate. Thus, as the release vehicle traverses the route and reaches a release point, the release vehicle activates an insect release mechanism to begin releasing mosquitoes at the rate associated with the release point.

The creation and positioning of individual release points is based on trap information obtained from the multiple insect traps 210a-g placed within the geographic region 200. For example, based on a number of captured insects of interest over a known period of time, the dynamic release planning system 110 determines an estimated wild insect population, such as by using extrapolation based on a ratio of trapped insects per wild population size.

After determining a wild insect population associated with each trap 210a-g, the dynamic release planning system 110 determines a number of modified insects, e.g., sterile male insects, to release for each estimated wild insect population. In this example, a number of modified insects, e.g., mosquitoes, is determined based on a pre-determined ratio of ten modified insects per one wild insect. In particular, the predetermined ratio in this example is ten sterile male insects for each wild female mosquito, though any suitable ratio may be employed, though typical ratios may be between 5 and 100 modified insects per relevant wild insect. Such ratios may vary based on, for example survivability of the modified insects, the expected population of wild insects of the same type as the modified insects, e.g., the wild population of male mosquitoes or a ratio of wild male to wild female insects of the relevant type, the expected weather (e.g., temperature, precipitation, wind, sunlight, etc.) at the time of release or within a predefined duration following release, etc.

In addition to determining a number of modified insects to release, a density and locations for the releases may be determined based on an area associated with each insect trap. For example an insect trap may be designed or expected to provide population information for an area within a radius of approximately 300 yards of the trap. Thus, the trap information may be used to determine both a number of modified insects to release as well as a number to release within a particular area.

Based on the determined number of modified insects for each trap 210a-g, the dynamic release planning system 110 determines a number of release points, a number of insects per release point, and a rate of release of modified insects. In this example, the number of insects per release point is fixed, thus, a number of release points may be determined by dividing the number of modified insects to release per trap into the number of insects per release point. Further, depending on a spacing between houses, in this example, and a vehicle speed along a portion of the route, the dynamic release planning system 110 can determine a release rate for the release point.

Further, after determining a release plan as discussed above, the dynamic release planning system 110 may iteratively adjust the number and placement of release points as new insect information is received from one or more of the insect traps 210a-g. For example, the dynamic release planning system 110 may wirelessly receive trap data every six hours from several traps, while it may receive manually entered insect information from other traps at irregular intervals. Thus, the dynamic release planning system 110 may generate a release plan based on the wirelessly received insect information, but may modify the release plan after receiving the manually entered insect information. Further, as additional insect information is received from traps over time, e.g., multiple samples from one trap may be received between the times a release vehicle traverses a route.

In this example, the release points are spaced evenly along the route, with the exception of release points 610h and 610i, which are spaced such that release point 610e is approximately equidistant between 610h and 610i, though 610e is a release point as the release vehicle traverses the route between release point 610d to release point 610f. However, despite the even spacing of the release points, different release points may have different release rates. In this example, the dynamic release planning system 110 establishes release rates based on a number of houses near a release point. Thus, for houses that are spaced farther apart, the release rate per distance travelled is lower than for houses that are closely spaced. Distances between adjacent houses along the route may be obtained from United States Geological Survey ("USGS") information, local city or county plat maps, a map service, such as Google® Maps®, etc.

Based on a specified release rate at a release point 610a-i, the release vehicle may adjust the rate at which one or more segments of an insect container are presented to a blower 408 and opening 406, or it may throttle the blower speed to reduce or increase the number of insects blown from the insect container segment(s). Thus, in this example, each release point 610a-i indicates a point at which to begin releasing insects rather than a location where an entire population of insects is released. However, in some examples, a release location may indicate that the release vehicle should stop and release the specified number of insects at the specific release location.

Figure 7:
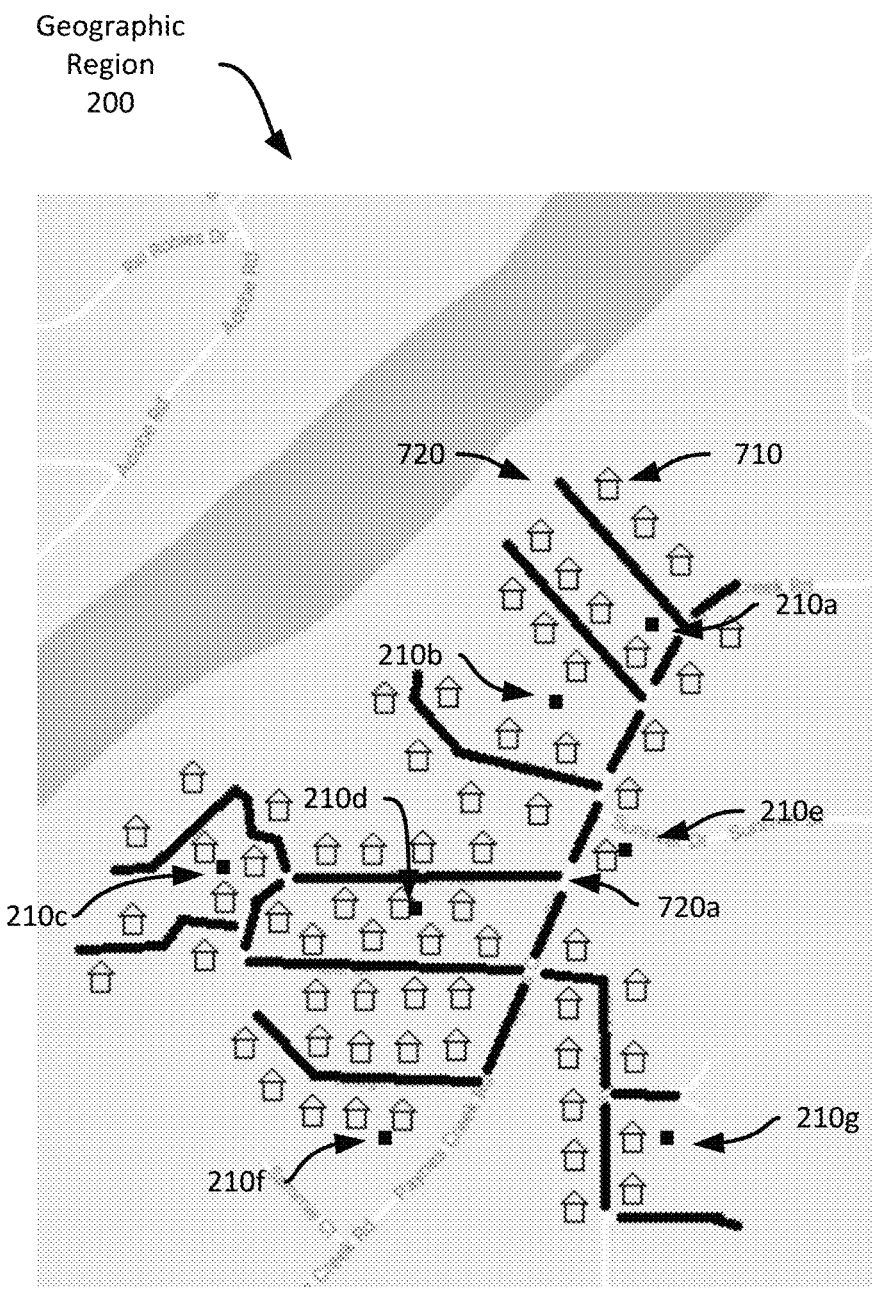
FIG. 7 shows an example geographic region having insect traps and multiple road segments.

It should be appreciated that release locations may be selected according to different techniques. For example, release locations may be selected based on a density of houses along various streets within the geographic region. Referring now to FIG. 7, FIG. 7 shows the example geographic region 200 of FIG. 2 having a number of roads and houses 710, in addition to the insect traps 210a-g. In addition, the roads have been divided into road segments 720, where each segment begins or ends at an intersection of two (or more) roads. Thus, the road segments have different lengths and, consequently, differing numbers of houses adjacent to each.

In this example, release locations may be determined based on house locations and corresponding road segments, as well as the trap information obtained from the various insect traps 210a-g as discussed above. After obtaining trap information as discussed above, a wild insect population per house may be determined with respect to each trap and the houses within a predetermined radius of the nearest trap. Thus, each house 710 may have a different number of wild insects associated with it, depending on which trap is nearest and the number of nearby houses. For example, trap 210g may encompass seven houses, while trap 210d may encompass fifteen houses. Based on the respective estimated wild insect population at each trap, the number of wild insects per house may be determined.

After determining the number of wild insects per house, each house may be associated with a corresponding road segment. A corresponding road segment may be determined, for example, by determining which of two roads each house is nearer. Alternatively, the street address for each house may be used to determine a corresponding road segment. In some examples, satellite image data or manual reconnaissance may be used to determine a road segment that connects to a house's driveway, which may then be assigned as the corresponding road segment.

After each house 710 has been assigned to a road segment, each road segment may be weighted based on the number of houses and the number of wild insects per assigned house. For example, the total estimated wild population may be divided into the respective share of the wild insect population assigned to the houses for each corresponding road segment. The weights may then be used to determine a placement of one or more release locations (or no release locations) along each road segment. For example, based on a total wild insect population within the geographic region 200, a total number of modified insects may be determined, as discussed above. Further, based on the trap information for the individual traps, a number of modified insects to be released per trap may be determined in a similar way. For each road segment, the associated houses have respective corresponding number of wild insects, as discussed above, thus a number of insects to be released per house along a road segment may be determined. Based on a time to release (or a release rate for) a number of modified insects, one or more release points along a road segment may be allocated.

In this example, the geographic region has a total wild female mosquito population of 20,000, thus, a total of 200,000 sterile male insects are to be released in an initial wave, using a predetermined ratio of 10:1 sterile males. Considering one road segment 720a adjacent to trap 210d, a total of seven houses are associated with the road segment 720a. The trap 210d indicates a wild insect population of 6,000 wild female mosquitoes, thus, of the fifteen houses within the trap's coverage area, each house has 400 wild female mosquitoes. Thus, for the seven houses adjacent to the road segment, the road segment has a weight of 0.14 (2,800 divided by 20,000), meaning a total of substantially 14% of the 200,000 sterile male insects to be released should be released along the road segment 720a. Thus, 28,000 sterile male mosquitoes must be released. In this example, each release location can accommodate releasing a maximum of approximately 15,000 sterile male mosquitoes. Thus, the road segment should have at least two release points. In this example, release points may be evenly spaced within a particular road segment. Though in some examples, each individual house may have its own weight which may bias the location of one or more release points based on the locations and relative spacing of the various houses within the geographic region.

Figure 8:
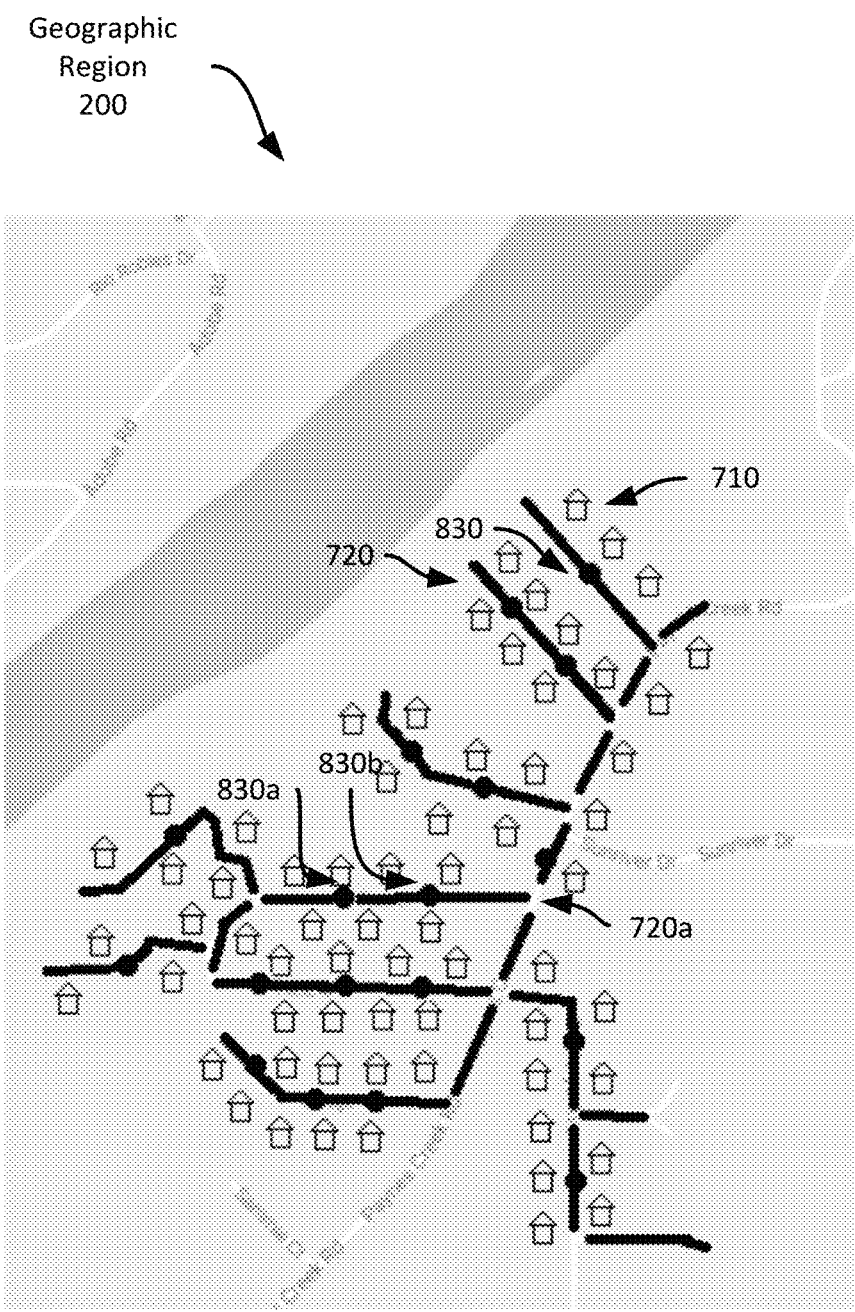
FIG. 8 shows an example geographic region having insect traps, multiple road segments, and multiple insect release points.

Referring to FIG. 8, FIG. 8 shows the geographic region with release points 830 assigned to each road segment 720. As can be seen, road segment 720a has been assigned two release points 830a-b that substantially equally divide the road segment 720a into thirds. In addition, release points have been assigned to other road segments within the geographic region 200. Further, it should be noted that some road segments may have no assigned release locations, which may occur when a road segment has no corresponding houses, a weight assigned to the road segment is below a predetermined threshold, e.g., 0.01, a length of a road segment is below a predetermined value, e.g., 250 feet, etc.

Figure 9:
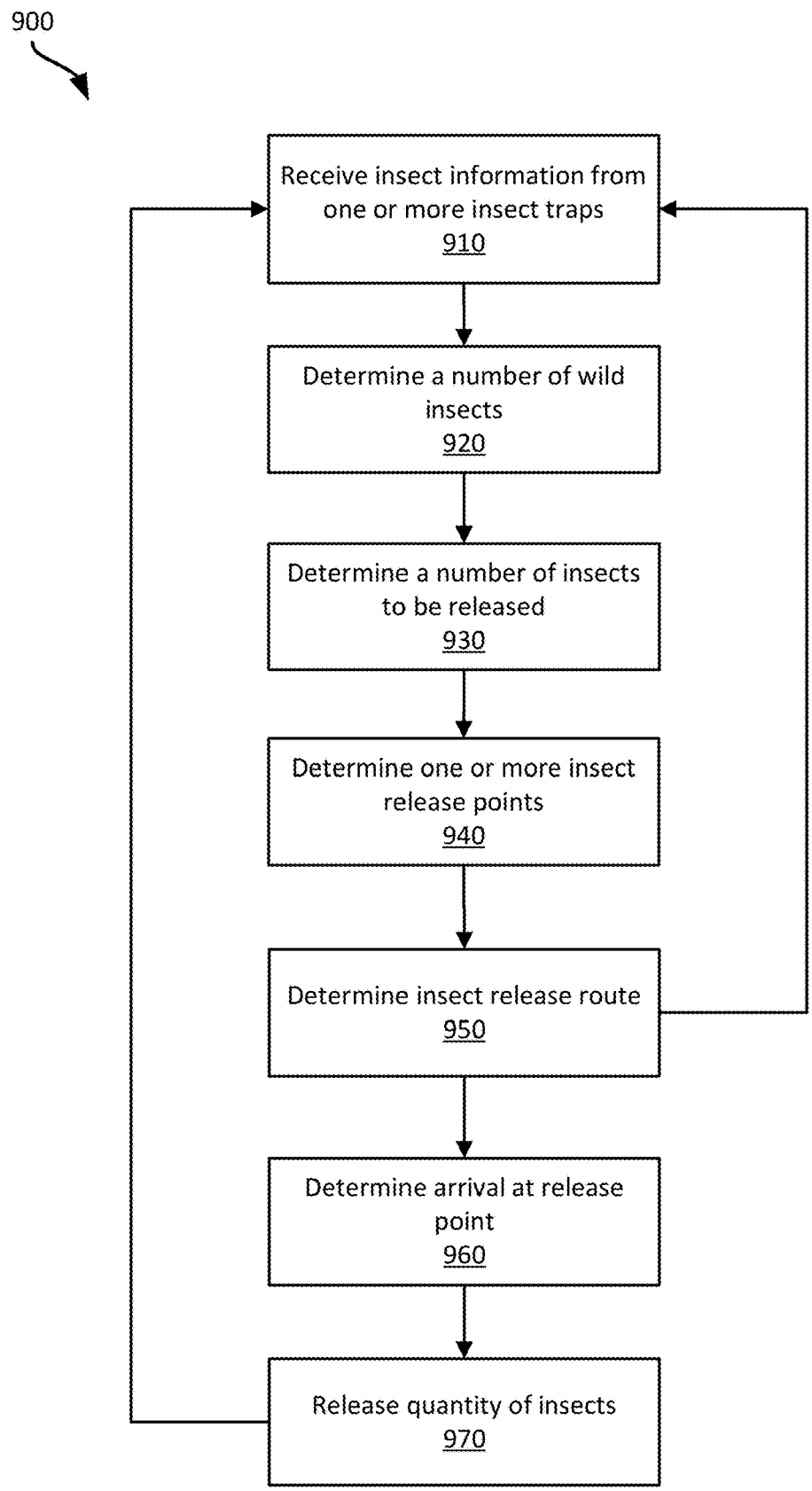
FIG. 9 shows an example method for dynamic release planning for insect release.

Referring now to FIG. 9, FIG. 9 shows an example method 900 for dynamic release planning for insect release. The method 900 will be discussed with respect to the system described in FIG. 1; however, any suitable system according to this disclosure may be employed.

At block 910, the dynamic release planning system 110 receives insect information from a set of one or more insect traps 120a-n. As discussed above, the insect information may be received autonomously, such as via wireless or wired data transfer from one or more of the traps. In some examples, insect information may be obtained manually from one or more traps and inputted into the dynamic release planning system 110. Insect information may include a number of insects of interest captured by a trap, e.g., a number of wild female *Aedes aegypti* mosquitoes. It may also include a number of male or female insects captured, a number of eggs or a number of hatched eggs, etc.

In some examples, the dynamic release planning system 110 may also obtain weather information from a weather system 140 or epidemiology information from an epidemiology system 150 as discussed above with respect to FIG. 1.

It should be appreciated that insect information, weather information, epidemiology information, etc. may be received at block 910 at any time during performance of the method 900 or may be received at different times from different insect traps 120a-n. Thus, while depicted as a single discrete block 910, insect information may be obtained in real time from one or more of the traps 120a-n.

At block 920, the dynamic release planning system 110 determines a number of wild insects associated with one or more of the insect traps 120a-n. For example, the dynamic release planning system 110 may determine a number of wild insects associated with each trap from which insect information was received.

At block 930, the dynamic release planning system 110 determines a number of insects to be released. As discussed above, a number of insects to be released may be based on a predetermined ratio of wild insects to modified insects. For example, a ratio of 10:1 may be employed as a default ratio. In some examples, other ratios may be employed. Further, on successive iterations of the method 900, the ratio may be modified.

For example, the dynamic release planning system 110 may assess a modified insect survivability based on the trap information. As discussed above, a total insect population may be estimated based on the trap information. Thus, if a modified insect population indicates low survivability, e.g., a mortality rate of 25% per day, the system 100 may increase the ratio based on the survivability.

Further, in some examples, each release of modified insects may be interpreted as a "dose" of insects. Thus, based on a mortality rate, the dose of modified insects may be adjusted to maintain a minimum concentration of modified insects within an environment. Thus, determining a number of insects to be released may be based on a predetermined minimum population of modified insect within the geographic region, within a trap's coverage area, per house, etc. Thus, a population of modified insects may be modeled using a "decay" based on mortality rate of the modified insects and thus, an initial dose of modified insects may be selected such that the modified insect population decays to value above the minimum population number before the next dose of modified insects is released into the geographic region.

It should be appreciated that the minimum population of modified insects may be adjusted based on a population of wild insects. For example, as the wild population decreases due to the released "doses" of modified insects, the dose size may be correspondingly reduced, such as to maintain at least a minimum ratio of modified insects to wild insects within the geographic region.

At block 940, the dynamic release planning system 110 places one or more insect release points on the route. In this example, the dynamic release planning system 110 determines a number of insect release points for each insect trap 210*a-g* based on the determined number of wild insects. In this example, the dynamic release planning system 110 is configured to release a number of modified insects that is approximately ten times the number of wild insects of interest, e.g., male mosquitoes. Thus, if a trap indicates a wild insect population as having approximately 500 individuals, the dynamic release planning system 110 may establish that approximately 5000 insects should be released in proximity to the trap. The dynamic release planning system 110 may then determine a number of modified insects to release with respect to each trap.

The dynamic release planning system 110 may then determine a number of insects to release per release point. In this example, the dynamic release planning system 110 uses a fixed number of modified insects per release point based on the style of release mechanism employed. The dynamic release planning system 110 then establishes one or more release points for each trap based on the number of modified insects to be released per release point and the number of modified insects to be released for each trap.

However, in some examples, rather than generating new release points, the dynamic release planning software 110 may obtain prior release points for a route and slightly perturb the locations of one or more of the release points. Such perturbations may help ensure an even distribution of insects across the route. For example, if release points remain static over time, characteristics of the release mechanism, release vehicle, etc., may result in areas along the route where fewer than a desired number of insects are released. However, by perturbing the locations of the previously defined release points, such characteristics may be averaged out over time.

In this example, after establishing the release points, the dynamic release planning system 110 in this example places each established release point at a position that is approximately evenly spaced along the length of the route. Thus, the distance between subsequent release points may be the same or substantially the same. However, in some examples the release points may be placed according to characteristics of the region traversed by the route. For example, release points may be placed based on the presence of hills, valleys, ravines, marshes, swamps, swimming pools, lakes, ponds, etc. within a geographic region of interest.

In some examples, release points may be selected or adjusted based on extant weather along the route. For example, if a release vehicle is scheduled to depart within a period of approximately 30 minutes, the dynamic release planning system 110 may iterate through the method 900 and employ then-current weather conditions in determining the placement of one or more release points along the route, a number of insects to release at one or more release points, or a number of insects to release in total along the route. Other factors, such as time of day may be employed as well.

In some examples, release points may be placed or adjusted based on human populations along the route. For example, one or more release points may be placed based on the location of one or more houses along the route, a number of houses per unit area along a portion of the route, changes in human population density along the route, etc. Still other factors may be employed in some example, including the type of release vehicle. For example, cars, trucks, or sport utility vehicles ("SUV") may have greater capacities and release rates than others, such as motorcycles, bicycles, or even a person on foot. In some examples, release may accomplished by boat or by aircraft. Suitable aircraft may include airplanes, helicopters, etc. that have on-board human crew members. Other aircraft may be unmanned or remotely-piloted, such as drones, blimps, balloons, etc.

The type of release vehicle used may affect placement of release points or a number of insects released at a particular release point. For example, if the vehicle is car, truck, SUV, etc., release points may be placed alongside or on a road surface. Other types of vehicles may allow for release points at more geographically diverse locations, including off-road or other terrain that may easiest be reached by alternate modes of transport (e.g., bicycles, on foot, all-terrain vehicle, etc.), including by air or water. Similarly, insect population capacity may vary based on the type of vehicle. For example, a truck or van may be able to carry a considerably larger population of insects (and a more complex release mechanism), than a person on foot. Further, different vehicles may have different heights of release for the insects. Aircraft may release at tens or hundreds of feet off of the ground, while ground vehicles may release between two and ten feet off of the ground (or lower or higher, depending on the release mechanism, vehicle type, etc.).

As discussed above with respect to FIGS. 7 and 8, in some examples, one or more road segments within a geographic region may be identified and assigned weights based on corresponding houses and wild insect populations. One or more (or no) release points may be assigned to each road segment based on the assigned weights as discussed above.

At block 950, the dynamic release planning system 110 generates a route through a geographic area associated with the set of one or more traps 120*a-n*. In this example, the dynamic release planning system 100 generates a route through the geographic area that intersects each of the established release points. In one example, the route may be predetermined; however, in some examples, the dynamic release planning system 110 may generate a route to traverse a route on roads adjacent to the locations of the respective traps 120*a-n*. For example, as can be seen in FIG. 3, the route 310 traverses multiple roads that are adjacent to the locations of each of the traps 210*a-g*.

After generating the route, the route may be provided to a release vehicle, which may traverse the route and release the specified number of modified insects. The method 900 may then be repeated at a later date after obtaining further insect population information. Subsequent iterations may adjust one or more predetermined ratios or values, e.g., a ratio of modified insects to wild insects, a minimum modified insect population, etc. Thus, over multiple successive iterations, a wild insect population may be reduced or eliminated.

At block 960, the release vehicle traverses the route and determines that it has arrived at release point. For example, the release vehicle may employ a positioning system, such as GPS, cellular positioning, Wi-Fi positioning, etc., or it may detect proximity to one or more traps based on a radio frequency beacon associated with the trap.

At block 970, the release vehicle releases a quantity of modified insects associated with the release point. For example, the release vehicle may activate a release mechanism, such as the example shown in FIGS. 4A-B and 5. The release mechanism may activate a blower and actuate the insect storage container 402 to sequentially expose insect chambers to the blower and to blow insects into the wild. In this example, the insect chambers are filled with a predetermined number of insects, which may enable the insect release system to release a known number of insects per insect chamber, thereby allowing a precise dosing of modified insects.

Figure 10:
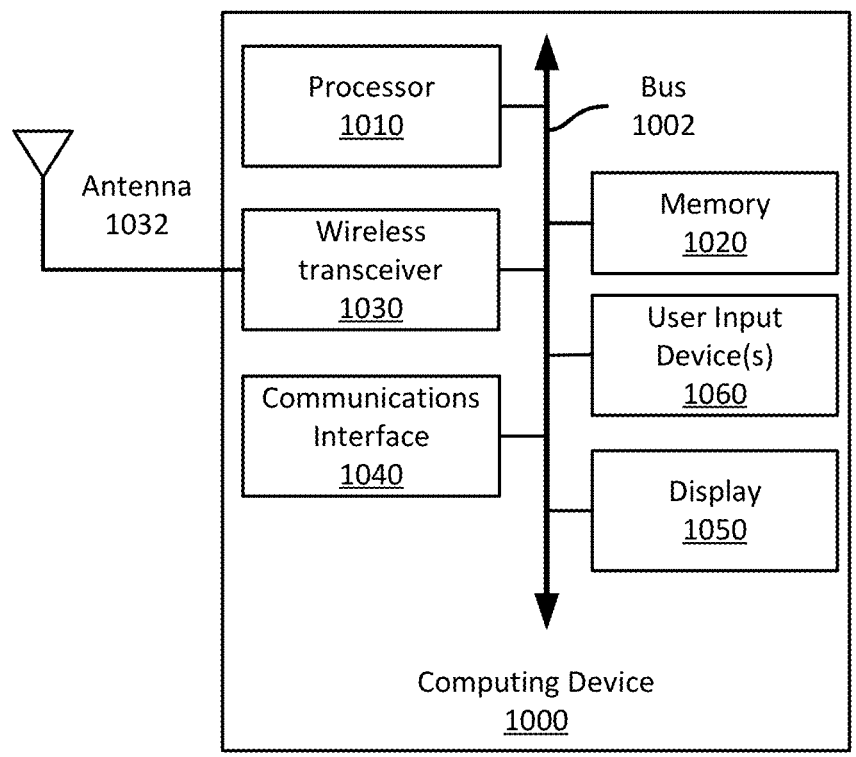
FIG. 10 shows an example computing device suitable for use with one or more systems or methods for dynamic release planning for insect release.

Referring now to FIG. 10, FIG. 10 shows an example computing device 1000 suitable for use with one or more systems or methods for dynamic release planning for insect release according to this disclosure. The example computing device 1000 includes a processor 1010 which is in communication with the memory 1020 and other components of the computing device 1000 using one or more communications buses 1002. The processor 1010 is configured to execute processor-executable instructions stored in the memory 1020 to perform insect sensing according to different examples, such as part or all of the example method 900 described above with respect to FIG. 9. The computing device, in this example, also includes one or more user input devices 1070, such as a keyboard, mouse, touchscreen, microphone, etc., to accept user input. The computing device 1000 also includes a display 1060 to provide visual output to a user.

The computing device 1000 in this example also includes a wireless transceiver 1030 and corresponding antenna 1032 to allow the computing device 1000 to communicate wirelessly using any suitable wireless communication protocol, including WiFi, Bluetooth ("BT"), cellular, etc. techniques. The computing device 1000 also includes a communications interface 1040 that enables communications with external devices, such as a communications network. In some examples, the communications interface 1040 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   receiving insect information indicating a population of wild insects within a geographic region, the insect information obtained from one or more insect traps (120a-n) within the geographic region;

for each insect trap, determining a number of wild insects per street address within a predetermined radius of the respective insect trap based on the insect information;

determining one or more road segments of one or more roads based on the numbers of wild insects per address and locations of addresses along the one or more roads;

determining, based on the one or more road segments and the one or more street addresses, one or more insect release points based on the number of wild insects per unit area, each of the insect release points indicating a release of a predefined quantity of insects and a predetermined release rate; and generating an insect release route through the geographic region, the insect release route passing through each of the insect release points.

2. The method of claim 1, further comprising:

determining a number of houses in the geographic region;

determining a number of insect release points based on a predetermined ratio of wild insects per house; and wherein:

the determining the number of wild insects per unit area comprises determining a number of wild insects per house; and the placing the one or more insect release points comprises placing the number of insect release points.

3. The method of claim 2, further comprising:

determining centroids of a plurality of houses within the geographic region;

for each house of the plurality of houses, determining a road segment within the geographic region corresponding to the respective house;

determining a weight for each road segment based on the respective corresponding houses; and wherein the placing the one or more insect release points comprises determining an even distribution of the one or more insect release points based on the weights and the road segments.

4. The method of claim 1, further comprising:

determining a number of wild female insects per unit area;

determining a quantity of sterile male insects based on the number of wild female insects and a predetermined ratio.

5. The method of claim 1, further comprising:

receiving information indicating a number of trapped sterile male insects captured by one or more insect traps within the geographic region;

determining a longevity of sterile male insects previously released into the geographic region based on the number of trapped sterile male insects;

determining a quantity of sterile insects to release at each release point based on the longevity of sterile male insects.

6. The method of claim 1, wherein the insect release route indicates a travel speed of a release vehicle.

7. The method of claim 1, further comprising providing the insect release route to a release vehicle.

8. The method of claim 1, further comprising:

detecting arrival at a first insect release point of the one or more insect release points; and activating an insect release mechanism.

9. The method of claim 8, wherein the insect release mechanism comprises a tube having a population of insects and a blower; and wherein activating the release mechanism comprises:

activating the blower, presenting a portion of the tube to the blower, and moving the tube past the blower.

10. The method of claim 9, further comprising varying the movement of the tube past the blower based on a determined insect release rate.

11. The method of claim 1, further comprising, after generating the insect release route:

receiving additional information indicating an updated population of wild insects;

determining an updated number of wild insects per unit of area;

adjusting a placement of at least one insect release point; and updating the insect release route based on the adjusting.

12. The method of claim 1, wherein each insect release point has the same predefined quantity of insects.

13. The method of claim 1, wherein the generating the insect release route is based on a type of release vehicle.

14. The method of claim 13, wherein the type of release vehicle is one of (i) a truck or sport utility vehicle, (ii) a motorcycle, (iii) a car, (iv) a drone, (v) a manned aircraft, (vi) a bicycle, or (vii) a person.

15. The method of claim 1, wherein the generating the insect release route is based on one or more of (i) weather data, (ii) population density, (iii) building types within the geographic region, (iv) expected release height of the insect population, or (v) expected time of day of release.

16. A non-transitory computer-readable medium comprising processor-executable instructions configured to cause a processor to:

receive insect information indicating a population of wild insects within a geographic region;

for each insect trap, determine a number of wild insects per street address within a predetermined radius of the respective insect trap based on the insect information;

determine one or more road segments of one or more roads based on the numbers of wild insects per street address and locations of street addresses along the one or more roads;

determine, based on the one or more road segments and the one or more street addresses, one or more insect release points based on the number of wild insects per unit area, each of the insect release points indicating a release of a predefined quantity of insects and a predetermined release rate; and generate an insect release route through the geographic region, the insect release route passing through each of the insect release points.

17. The non-transitory computer-readable medium of claim 16, further comprising processor-executable instructions configured to cause a processor to:

determine a number of houses in the geographic region;

determine a number of insect release points based on a predetermined ratio of wild insects per house;

determine a number of wild insects per house; and place the number of insect release points.

18. The non-transitory computer-readable medium of claim 17, further comprising processor-executable instructions configured to cause a processor to:

determine centroids of a plurality of houses within the geographic region;

for each house of the plurality of houses, determine a road segment within the geographic region corresponding to the respective house;

determine a weight for each road segment based on the respective corresponding houses; and determine an even distribution of the one or more insect release points based on the weights and the road segments.

19. The non-transitory computer-readable medium of claim 16, further comprising processor-executable instructions configured to cause a processor to:
    determine a number of wild female insects per unit area;
    determine a quantity of sterile male insects based on the number of wild female insects and a predetermined ratio.

20. The non-transitory computer-readable medium of claim 16, further comprising processor-executable instructions configured to cause a processor to:
    receive information indicating a number of trapped sterile male insects captured by one or more insect traps within the geographic region;
    determine a longevity of sterile male insects previously released into the geographic region based on the number of trapped sterile male insects;
    determine a quantity of sterile insects to release at each release point based on the longevity of sterile male insects.

21. A system comprising:
    a non-transitory computer-readable medium; and
    a processor configured to execute processor-executable instructions stored in the non-transitory computer-readable medium, the processor-executable instructions configured to cause a processor to:
    receive insect information indicating a population of wild insects within a geographic region;
    for each insect trap, determine a number of wild insects per street address within a predetermined radius of the respective insect trap based on the insect information;
    determine one or more road segments of one or more roads based on the numbers of wild insects per street address and locations of street addresses along the one or more roads;
    determine, based on the one or more road segments and the one or more street addresses, one or more insect release points based on the number of wild insects per unit area, each of the insect release points indicating a release of a predefined quantity of insects and a predetermined release rate; and
    generate an insect release route through the geographic region, the insect release route passing through each of the insect release points.

22. The system of claim 21, wherein the processor is further configured to execute processor-executable instructions configured to cause a processor to:
    determine a number of houses in the geographic region;
    determine a number of insect release points based on a predetermined ratio of wild insects per house;
    determine a number of wild insects per house; and
    place the number of insect release points.

23. The system of claim 22, wherein the processor is further configured to execute processor-executable instructions configured to cause a processor to:
    determine centroids of a plurality of houses within the geographic region;
    for each house of the plurality of houses, determine a road segment within the geographic region corresponding to the respective house;
    determine a weight for each road segment based on the respective corresponding houses; and
    determine an even distribution of the one or more insect release points based on the weights and the road segments.

24. The system of claim 21, wherein the processor is further configured to execute processor-executable instructions configured to cause a processor to:
    determine a number of wild female insects per unit area;
    determine a quantity of sterile male insects based on the number of wild female insects and a predetermined ratio.

25. The system of claim 21, wherein the processor is further configured to execute processor-executable instructions configured to cause a processor to:
    receive information indicating a number of trapped sterile male insects captured by one or more insect traps within the geographic region;
    determine a longevity of sterile male insects previously released into the geographic region based on the number of trapped sterile male insects;
    determine a quantity of sterile insects to release at each release point based on the longevity of sterile male insects.

* * * * *